US00PP26159P3

(12) United States Plant Patent
Korlipara

(10) Patent No.: US PP26,159 P3
(45) Date of Patent: Nov. 24, 2015

(54) ***ECHINACEA* PLANT NAMED 'BIG KAHUNA'**

(50) Latin Name: ***Echinacea* hybrid**
Varietal Denomination: Big Kahuna

(71) Applicant: Terra Nova Nurseries, Inc., Canby, OR (US)

(72) Inventor: Harini Korlipara, Canby, OR (US)

(73) Assignee: Terra Nova Nursuries, Inc., Canby, OR (US)

( * ) Notice: Subject to any disclaimer, the term of this patent is extended or adjusted under 35 U.S.C. 154(b) by 185 days.

(21) Appl. No.: 13/987,234

(22) Filed: Jul. 12, 2013

(65) Prior Publication Data

US 2015/0020277 P1 Jan. 15, 2015

(51) Int. Cl.
*A01H 5/00* (2006.01)

(52) U.S. Cl.
USPC ..... Plt./428

(58) Field of Classification Search
USPC ..... Plt./428
CPC ..... A01H 5/025; A01H 5/02
See application file for complete search history.

(56) References Cited

PUBLICATIONS

Greenhouse Grower Mar. 2013.*

* cited by examiner

*Primary Examiner* — Keith O. Robinson
(74) *Attorney, Agent, or Firm* — Klarquist Sparkman, LLP

(57) ABSTRACT

A new and distinct *Echinacea* plant named 'Big Kahuna' characterized by large inflorescences of melon orange to bicolor melon orange and peach ray florets, red orange cones, early bloom time, a compact, upright habit with excellent stem count, and excellent vigor.

1 Drawing Sheet

Botanical denomination: *Echinacea* hybrid.
Variety designation: 'Big Kahuna'.

BACKGROUND OF THE INVENTION

The present invention relates to a new and distinct cultivar of *Echinacea* and given the cultivar name 'Big Kahuna'. *Echinacea* is in the family Asteraceae. This new cultivar is a seeding originating from a planned breeding program. The exact parents of this selection are unknown, unnamed, proprietary plants.

This new *Echinacea* cultivar is distinguished by:

1. large inflorescences of melon orange to bicolor melon orange and peach ray florets,
2. red orange cones,
3. early bloom time,
4. a compact, upright habit with excellent stem count, and
5. excellent vigor.

Compared to *Echinacea* 'Flame Thrower' (U.S. Plant Pat. No. 21,932), the new cultivar is a smaller plant, the inflorescences are larger, and the flower color is bicolor melon orange and peach rather than red and orange.

Compared to *Echinacea* 'Katie Saul' (U.S. Plant Pat. No. 18,783), the new cultivar has larger flowers, shorter habit, and ray florets of bicolor melon orange and peach rather than soft peach and rose.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a two-year-old plant of *Echinacea* 'Big Kahuna' growing in the trial field in full sun in early July in Canby, Oreg. A black background was held behind the plant to show it more clearly.

FIG. 2 shows a close up of the flower on the same plant.

DETAILED PLANT DESCRIPTION

The following is a detailed description of the new *Echinacea* cultivar based on observations of 2-year-old specimens growing in the trial field in full sun in early July in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The Royal Horticultural Society Colour Chart, 5$^{th}$ edition, 2007.

Plant:

*Type*.—Herbaceous perennial.
*Hardiness*.—USDA Zones 4 to 9.
*Size*.—Grows to about 53 cm wide and 67 cm tall to top of inflorescences.
*Form*.—Upright, dense, basal clump, with about 13 stems from the base.
*Vigor*.—Excellent.

*Roots*.—Fibrous, with many downward growing and few laterals, ivory in color, Yellow White 158D, roots develop easily from cuttings from the crown.

Stem (flowering):

*Type*.—Ascending, with 1 to 5 inflorescences per stem.

*Size*.—To 64 cm tall to a terminal inflorescence and 12 mm wide at base.

*Internode length*.—1 cm to 5 cm.

*Surface texture*.—Strigose.

*Color*.—Yellow Green 146B.

Leaf (basal):

*Type*.—Simple (variegation absent).

*Shape*.—Lanceolate.

*Arrangement*.—Basal.

*Blade size*.—Grows to 13.5 cm long and 5.2 cm wide.

*Margins*.—Coarsely serrate.

*Apex*.—Acuminate.

*Base*.—Attenuate.

*Surface texture*.—Strigose on both sides, rugosity — medium, glossiness — matte.

*Venation*.—Pinnate, with 3 main veins from the base, Yellow Green N147A on top and bottom side.

*Color*.—Topside Green N137A, bottom side closest to Yellow Green 147B.

*Petiole description*.—Clasping, grows to 9 cm long and 5 mm wide above the clasp, sparsely strigose, Green N137A on sides and Yellow Green 147B in middle.

Leaf (stem):

*Type*.—Simple.

*Shape*.—Lanceolate.

*Arrangement*.—Alternate.

*Blade size*.—Grows to 12 cm long and 4 cm wide.

*Margins*.—Serrate.

*Apex*.—Acuminate.

*Base*.—Attenuate.

*Surface texture*.—Strigose on both sides.

*Venation*.—Pinnate, with 3 main veins from the base, Yellow Green N144D on top and Yellow Green 147C on bottom side.

*Color*.—Topside Green N137A, bottom side closest to Yellow Green 147B.

*Petiole description*.—On all but upper leaves, clasping, grows to 2.5 cm long and 3 mm wide above the clasp, sparsely strigose, Green N137A on sides and Yellow Green N144D in middle.

Inflorescence:

*Type*.—Composite on terminal stalked heads.

*Number of flowering stems from the ground*.—About 13.

*Floriferousness*.—Strong.

*Flowering stem*.—Grows to 64 cm tall from the base of the plant to the terminal inflorescence and can grow to 11 cm to 17 cm long from the top stem leaf to the base of an inflorescence; branched with 1 to 5 inflorescences per stem; diameter growing to 12 mm wide at the base; strigose; Yellow Green 146B.

*Size*.—Grows to 13.5 cm wide and 5 cm deep as disc enlarges.

*Form*.—Ray florets held slightly reflexed, mature disc is conic.

*Immature inflorescence*.—Grows to 5.5 cm wide and 2 cm deep, ray florets held at a 40 degree angle from the horizontal and rolled up so only the back color shows, Red 36B, disc color Yellow Green 146A.

*Ray florets*.—Without pistil or stamen, in one or two rows, 26 to 31 in outside row and to 16 to 22 in inside row, grow to 63 mm long and 11.5 mm wide, oblanceolate with the tip two to three-toothed (each acute), cup upwards, entire margins, base attenuate, glabrous on both sides; young topside Orange 26B, bottom side closest to Red 36A, maturing to Yellow Orange 22A on top ⅔ blending to Red 48B at the base, bottom side Red 35C.

*Disc*.—Flat becoming conic, growing to 35 mm deep and 42 mm wide with maturity, Orange 26 with background Purple N79A.

*Disc florets*.—About 420 in number, each with 1 pistil and 4 stamen, grow to 10 mm long and 2 mm wide, each with one persistent, very stiff linear bract (16 mm long with top ⅓ Orange 26B with tip Orange Red 34A, middle ⅓ Yellow Green 146B, bottom ⅓ White 155A); corollas 6 mm long and 3 mm wide, tubular with a bulbous base, 5 lobed, 0.5 mm long and 0.5 mm wide with margin entire, tips acute, glabrous on both sides, in and outsides Green 138A on tube and blending to Purple N79A at apex; pistil 12 mm long, ovary 4 mm long, White NN155A with Yellow Green 144A on top, style 5 mm long Green 138D, 2-branched stigma 1.5 mm long and spreading 3 mm, Greyed Purple 187A; stamen 5 mm long, filaments 2 mm long, threadlike, White 155A, anthers 3 mm long Greyed Purple 187A, pollen Orange 18A.

*Phyllaries*.—In 2 to 3 leafy series, area grows to 28 mm wide and 12 mm deep, lobes lanceolate in shape, reflexed, grow to 12 mm long and 4 mm wide, Green 137A, margins strigose, tip acute, strigose on both sides.

*Receptacle*.—Grows to 15 mm wide and 17 mm deep, White 155A.

*Bloom period*.—July through October in Canby, Oreg.

*Fragrance*.—Floral.

*Lastingness*.—Each inflorescence lasts about two weeks in Canby, Oreg.

*Seeds*.—Not seen.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *

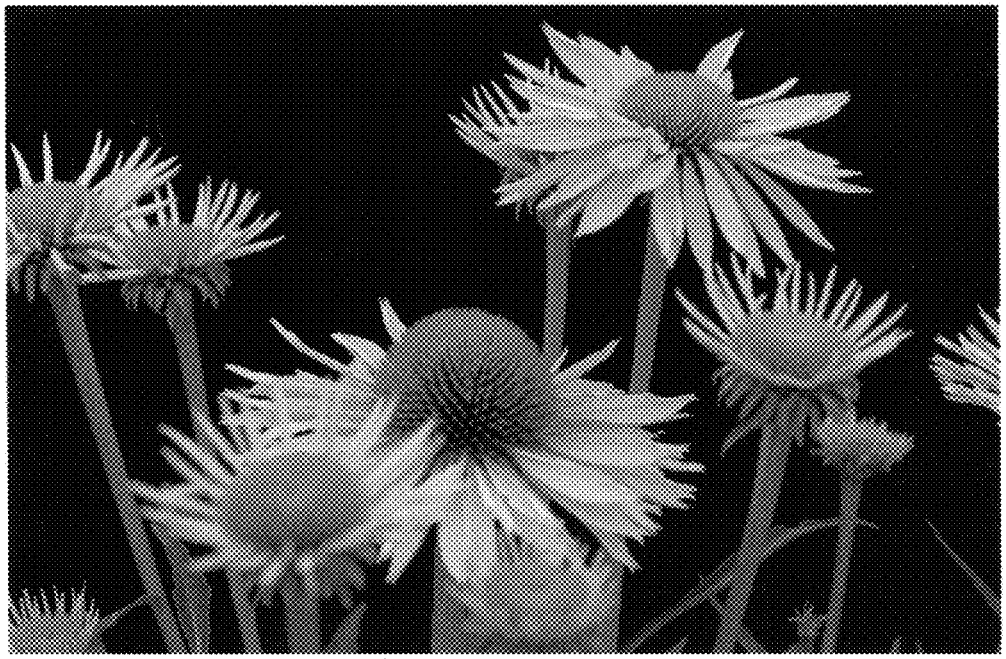

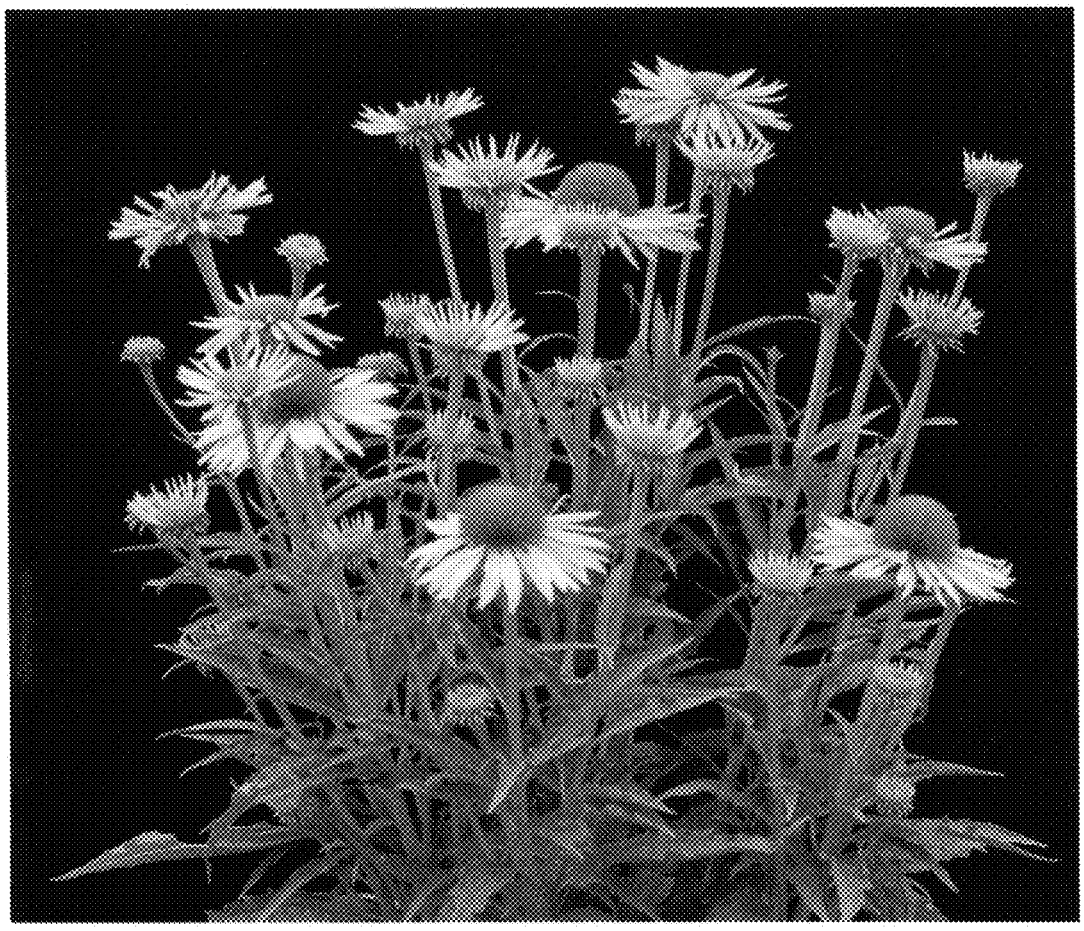
FIG. 1 above, FIG. 2 below